US006543933B2

(12) United States Patent
Stergiopoulos et al.

(10) Patent No.: US 6,543,933 B2
(45) Date of Patent: Apr. 8, 2003

(54) NON-INVASIVE 3-D INTRACRANIAL THERMOGRAPHY SYSTEM

(75) Inventors: Stergios Stergiopoulos, Toronto (CA); Nikolaos Uzunoglu, Athens (GR)

(73) Assignee: Her Majesty the Queen as represented by the Minister of National Defence of Her Majesty's Canadian Government, Ottawa (CA)

(*) Notice: Subject to any disclaimer, the term of this patent is extended or adjusted under 35 U.S.C. 154(b) by 0 days.

(21) Appl. No.: 10/046,547

(22) Filed: Jan. 16, 2002

(65) Prior Publication Data

US 2002/0126731 A1 Sep. 12, 2002

Related U.S. Application Data

(60) Provisional application No. 60/261,815, filed on Jan. 17, 2001.

(51) Int. Cl.[7] .............................. A61B 5/05; G01K 1/16
(52) U.S. Cl. ..................... 374/122; 374/120; 374/141; 600/430; 600/549
(58) Field of Search ......................... 374/120–122, 374/141, 163, 129; 600/549, 430; 324/637, 639, 642

(56) References Cited

U.S. PATENT DOCUMENTS

| | | | | |
|---|---|---|---|---|
| 4,416,552 A | * | 11/1983 | Hessemer, Jr. et al. | 374/117 |
| 4,627,442 A | * | 12/1986 | Land | 128/736 |
| 4,677,988 A | * | 7/1987 | Constant et al. | 128/736 |
| 4,798,215 A | * | 1/1989 | Turner | 128/804 |
| 5,097,844 A | * | 3/1992 | Turner | 128/804 |
| 5,341,814 A | * | 8/1994 | Van De Velde et al. | 128/736 |
| 5,807,257 A | * | 9/1998 | Bridges | 600/430 |
| 5,924,996 A | * | 7/1999 | Cho et al. | 600/549 |
| 6,061,589 A | * | 5/2000 | Bridges et al. | 600/549 |

FOREIGN PATENT DOCUMENTS

| | | | | |
|---|---|---|---|---|
| EP | 0294854 A2 | * | 1/1984 | G01R/29/08 |
| JP | 401139083 A | * | 5/1989 | A61N/5/06 |

OTHER PUBLICATIONS

PC Myers et al; "Microwave Thermography: Principles, Methods, and Clinical Application"; Jrn of Microwave Power 14(2), 1979, pp. 106–115.

J. Edrich; "Centimeter–and Millimeter–Wave Thermograph—A Survey on Tumor Detection"; Jrn of Microwave Power 14(2), 1979, pp. 95–104.

Kenneth L. Carr et al; "Dual–Mode Microwave System to Enhance Early Detection of Cancer"; IEEE Transactions on Microwave Theory and Techniques; vol. MMT–29, No. 3, Mar. 1981, pp. 256–260.

* cited by examiner

Primary Examiner—Diego Gutierrez
Assistant Examiner—G. Verbitsky
(74) Attorney, Agent, or Firm—Larson & Taylor, PLC

(57) ABSTRACT

A microwave thermography apparatus to measure temperatures within a dielectric body comprises a partial ellipsoidal cavity with an electrical conductive surface wherein the body can be located at one focus of the cavity. A microwave antenna located at a second focus of the cavity is connected to a radiometer. That radiometer amplifies and filters signals from the antenna before they are applied to a detector with the temperature of the body being determined from the voltage amplitude of the detected signals.

15 Claims, 6 Drawing Sheets

NON-INVASIVE 3-D INTRACRANIAL THERMOGRAPHY SYSTEM

CROSS REFERENCE TO RELATED APPLICATIONS

This application claims benefit of U.S. Provisional Application No. 60/261,815, filed on Jan. 17, 2001.

FIELD OF THE INVENTION

The present invention relates to microwave radiometry technology and, in particular, to an apparatus for non-invasively measuring temperature distribution within a human body including the human skull for brain intracranial diagnostic applications.

BACKGROUND TO THE INVENTION

Many researchers have proposed and used, to some extent, microwave radiometry technology to non-invasively measure temperature distribution within the human body during the past 30 years. The reason for this is the fact that microwaves in the frequency range of 1–5 GHz penetrate through human tissues sufficiently and also provide sufficient directivity to measure the temperature distribution within the body. One reason for proposing to use microwave radiometry technology is the failure of infrared (IR) thermography techniques to provide useful information for temperature distribution within a human body including the human skull for brain intracranial diagnostic applications. This is due to the fact that although the human body emits maximum radiation at infrared (IR) wavelengths, the very high attenuation of this radiation passing through tissues make the IR thermography techniques of only limited value.

A publication entitled "Microwave Thermography: Principles, Methods and Clinical Applications" by P. C. Myerst et al in the Journal of Microwave Power 14(2), 1979 (pages 105 to 115) describes one type of microwave thermography technology where an antenna in the form of 1×2 cm rectangular waveguide filled with a low-loss solid is placed flush against the skin. The human body, as P. C. Myerst et al indicated, emits thermal radiation with an intensity that is proportional to tissue temperature and that at microwave frequencies of 3 GHz, the intensity is reduced by a factor of $\approx 10^8$ from the maximum intensity at an IR wavelength of $\lambda = 10 \mu m$. A microwave radiometer, however, can detect radiation with that intensity and determine changes in temperature of less than 1° C. in the human body. Since microwave radiation can penetrate human tissue for distances of several centimetres, this allows for the detection of variations in subsurface temperature. P. C. Myerst et al reported building three different radiometers to use with the rectangular antenna which operated at 1.3, 3.3 and 6.0 GHz. Tests were performed on patients at 1.3 and 3.3 GHz with results being reported in the publication.

Another publication by J. Edrich on pages 95 to 104 of the same journal entitled "Centimeter- and Millimeter-Wave Thermography—A Survey on Tumour Detection" describes further thermography instrumentation which operate at centimeter (cm) and millimeter (mm) wavelengths that can directly measure subcutaneous temperature in a human body. In this publication, the radiometry involved remote sensing by focussed apertures like lenses or reflectors that focus the cm or mm wave into a horn antenna mounted on a scanner. The scanner can be moved in a raster fashion over a patient lying on a bed. J. Edrich indicates that this type of scanner is better suited for high frequencies because of the requirement for an aperture diameter of many wavelengths but that going to higher frequencies will decrease penetration. However, more power is received at higher frequencies because the beam becomes narrower. J. Edrich states on page 98 that "As compared to the contacting method at 3 GHz, remote sensing at 9 GHz therefore results in an incremental antenna temperature that is twice as large and a subcutaneous resolution area of less than one eight". J. Edrich then further states that "Centimeterwave radiometry at this frequency should therefore be well suited for remote and reproducible probing of subcutaneous temperatures."

Another publication by Kenneth Carr et al in the IEEE Transactions on Microwave Theory and Techniques, Vol. MTT-29, No. 3, March 1981 entitled "Dual-Mode Microwave System to Enhance Early Detection of Cancer" on pages 256 to 260 describes an active microwave transmitter to provide localized heating taking advantage of differential heating of a tumour with respect to surrounding tissue and a passive microwave radiometer to permit early detection of a cancer. In this system, the microwave radiometer frequency was chosen to be at 4.7 GHz whereas the microwave heating frequency was at 1.6 GHz.

The temperature distribution inside the human body including the human skull for brain intracranial diagnostic applications can be measured up to at least 5–7 cm depths with microwave radiometry. However, there is a practical problem in sensing the radiated intercranial thermal energy at microwave frequencies since this would require an array of microwave antennas to coherently integrate the scattered thermal energy and localize the source area inside the human brain.

SUMMARY OF THE INVENTION

It is an object of the present invention to provide a microwave radiometry apparatus that is able to non-invasively and more accurately measure the temperature distribution within dielectric bodies such as in a human body including the human skull for brain intracranial diagnostic applications.

A microwave thermography apparatus, according to one embodiment of the invention, for measuring a temperature distribution within a dielectric body, comprises an ellipsoidal cavity having an electrical conductive surface wherein said body can be located at one focus of said cavity, a microwave antenna being located at a second focus of said cavity, which antenna is connected to a radiometer that amplifies and filters signals detected by the antenna before those signals from the radiometer are applied to a detector connected to an output of the radiometer.

BRIEF DESCRIPTION OF THE DRAWINGS

Preferred embodiments of the invention will now be described in more detail with reference to the accompanying drawings, in which.

DESCRIPTION OF THE PREFERRED EMBODIMENTS

Figure 1:
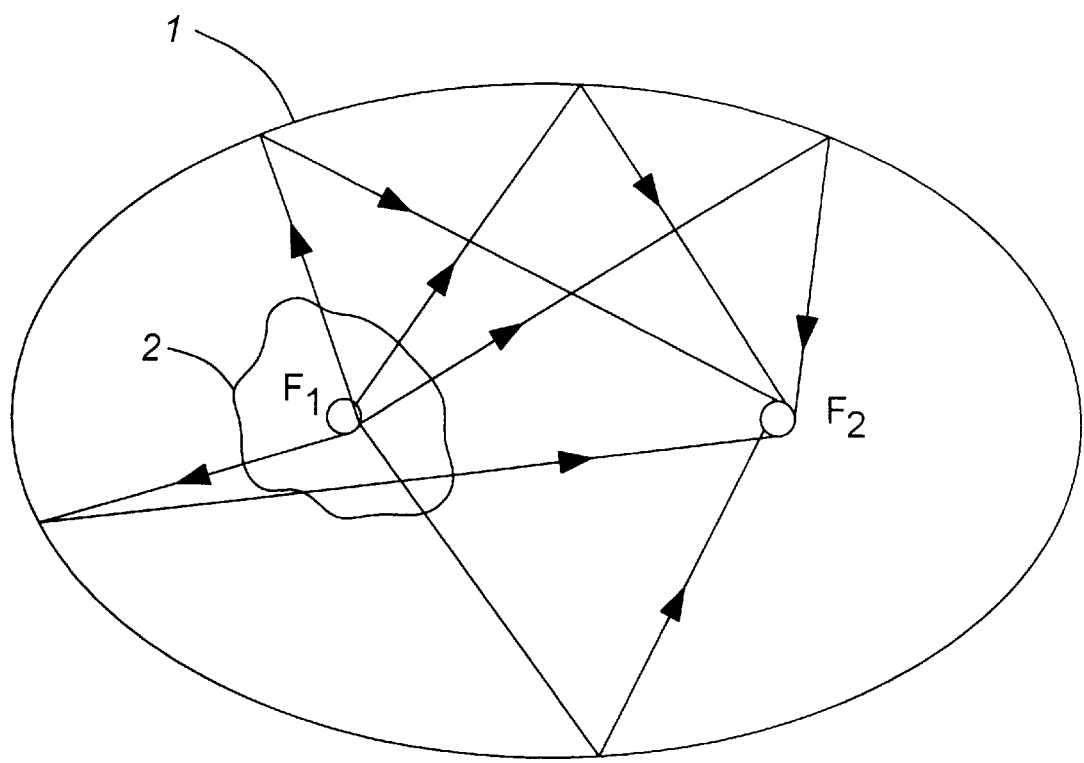
FIG. 1 is a diagram that illustrates the focusing properties of an ellipsoidal cavity.

During the past 30 years, many researchers have proposed and used, to some extent, microwave radiometry technology to measure temperature distribution in the human body, including the human skull for brain intracranial diagnostic applications, non-invasively. One reason for this is the failing of infrared (IR) thermography to provide any useful information for the temperature distribution within the human body since it is limited to the measurement of only the temperature at the skin's surface. The very high attenuation of IR radiation passing through tissues make IR thermography techniques of limited value. Microwaves in the frequency range of 1–6 GHz have sufficient penetration through human tissues to detect subcutaneous thermal abnormalities while, at the same time, providing satisfactory directivity to locate any abnormalities detected.

The amount of energy emitted by human tissues at microwave wavelengths is relatively small, reduced by about $10^8$ at 3 HGz, compared to the maximum intensity emission at 10 $\mu$m. The temperature distribution inside the human body and the human skull, however, can be measured up to at least 5–7 cm depths with microwave radiometry. There is a practical problem in sensing the radiated intracranial thermal energy at microwave frequencies with previous apparatus since this would require an array of microwave antennas to coherently integrate the scattered thermal energy and localize the source area inside the human brain.

There has been no method and/or apparatus that could provide, non-invasively, a three-dimensional temperature distribution deep within the human skull up to present. The technology described herein can, however, lead to an intracranial measurement ability up to 10 cm depth. The potential usefulness of mapping temperature inside the human brain, especially in the cortex, would be of very high value in phsychiatry, neurology and the prevention of heat stroke of the brain.

The intensity of the radiation field defines the requirement associated with the measurement of 3-D temperature inside a lossy medium. It can be shown that in order to have a satisfactory spatial resolution for a microwave thermography device, that:

$$\Gamma_A(r') \sim c_t \delta(r_A - r') \quad (1)$$

where $\Gamma_A(r')$ is the transfer function for the medium, $r_A$ is the antenna center coordinates, r' is the coordinates of the microwave originating area and $c_t = 3 \times 10^8$ m/sec is a constant. Then the analytical solution for the total radiated energy by the medium defined in (1) gives the intensity $$I = \frac{\omega_o^2 \mu_o k}{\pi} \Delta\omega \cdot c_t T(r_A) \sigma(r_A) \quad (2)$$

where:
- $\omega_o$ is the center frequency (in radians/sec) of the observed microwave spectrum bandwidth,
- $\mu_o$ is the magnetic permeability constant,
- k is Boltzaman's constant,
- $\Delta\omega$ is the bandwidth of observed microwave spectrum,
- $T(r_A)$ is the temperature spatial distribution within the medium of interest, and
- $\sigma(r_A)$ is the spatial distribution within the medium of interest for the electric conductivity.

The present invention can provide estimates of the product of $T(r_A)\sigma(r_A)$. Since the electric conductivity spatial distribution is approximately constant within the brain tissue structure, estimates of product term $T(r_A)\sigma(r_A)$ by the apparatus of the present invention will provide estimates of the temperature distribution within the intracranial cavity or any medium of interest. An exact assessment would require an extensive and rigorous analysis of the corresponding electromagnetic problem. Therefore, a geometrical optics approach is used herein to estimate the resolution properties of the present invention.

The present invention uses an ellipsoidal cavity with electrically conductive walls to achieve a maximum peak detection of the radiation pattern and a microwave antenna to measure the intensity of radiated microwaves from a dielectric body. It is a well known property that every ray originating from one focus of an ellipsoidal cavity will merge on the other focus with equal path lengths. This property of an ellipsoidal cavity 1 is illustrated in FIG. 1 where rays originated from a lossy medium 2 at one focus $F_1$ merge on the other focus $F_2$. In FIG. 1, it should be noted that all the rays originated from the focus $F_1$ pass through the focus $F_2$ keeping the same total path lengths following a single reflection from the ellipsoidal cavity walls. A sharp focus should arise at $F_2$ when a lossy medium is placed at $F_1$ while a receiving antenna is placed at $F_2$. Therefore, the use of an ellipsoidal (spheroidal) conductive wall cavity 1 essentially can be operated as a three dimensional BEAMFORMER.

In FIG. 1, taking the path of each ray emerging from the focal point $F_1$ and neglecting the reflection phenomena, it can be established that the spherical volume around the focus $F_1$ with radius of $\lambda_g/4$ ($\lambda_g$ being the wavelength inside the tissue) will be coherently contributed to the field at the point $F_2$. Considering the fact that for human brain tissue, the relative dielectric constant is approximately equal to $\in_r = 60$ (real part) then $$\lambda_g = \lambda/\sqrt{\in_r} \quad (3)$$

where $$\lambda = \frac{2\pi}{\omega_o} c$$

is the free space wavelength and $c = 3 \times 10^8$ m/s.

The selection of an operating frequency $f_o$ for measurement of intracranial thermal energy needs to be based on the penetration property of radiation through a human head. In order to design and test an apparatus according to the present invention, a frequency of 1.5 GHz or 3.5 GHz was considered to be suitable since a sufficient spatial resolution equal to 20 cm/$\sqrt{60} \cong 3$ cm is obtained while the penetration depth would be in the order of 6 to 10 cm. The selected frequency could, however, be from about 1.5 GHz to 3.5 GHz or other microwave frequencies.

The design of an ellipsoidal cavity as an experimental prototype to test the present invention was based on the above parameters. Considering the requirement for housing a test object and to keep the size of the cavity reasonable, the following dimensions were selected:
Major Axis Total Length=150 cm,
Minor Axis Total Length=120 cm with an interfocal distance of 90 cm.

Figure 7:
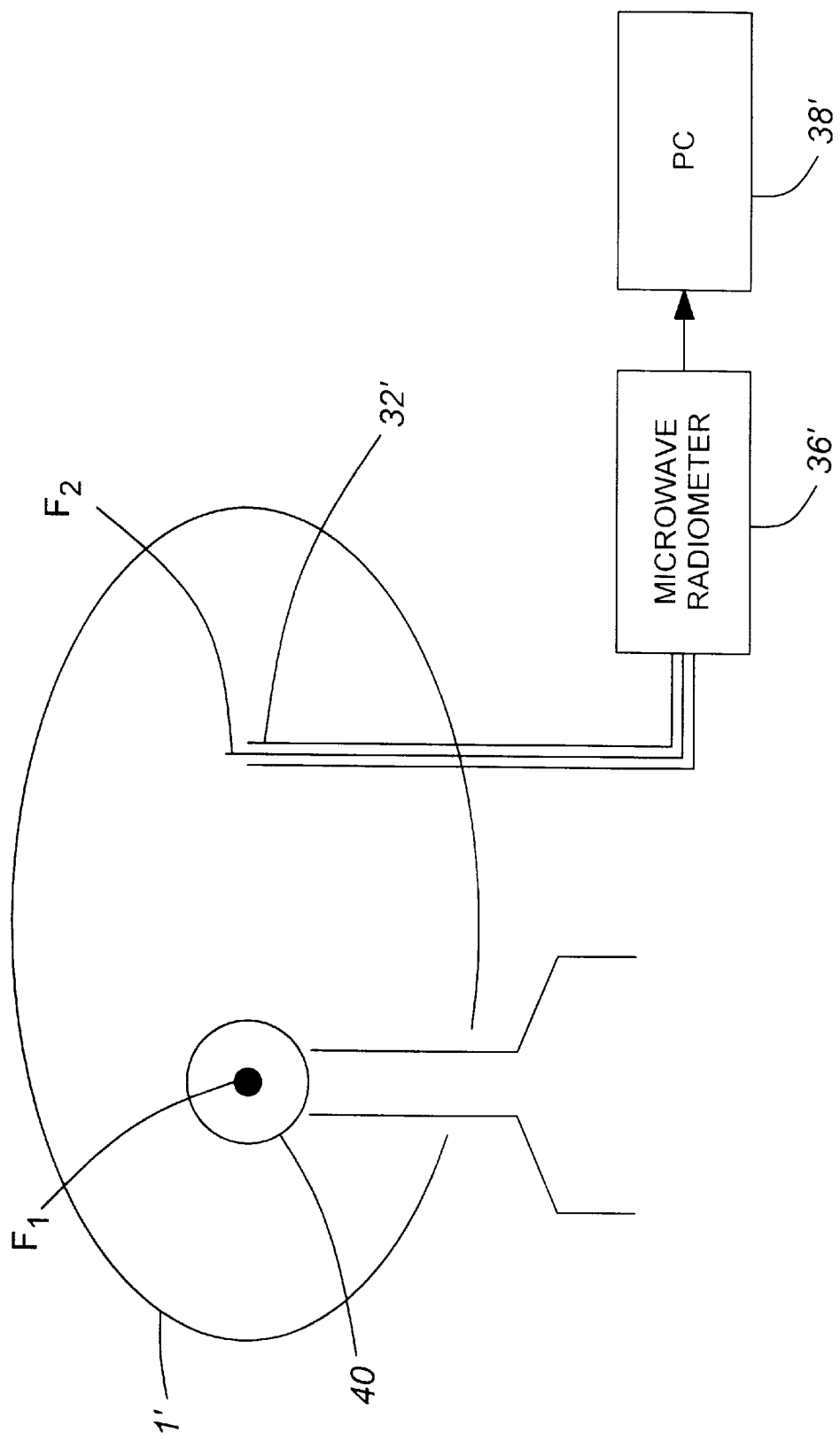
FIG. 7 is a block diagram of an intra-cranial temperature mapping system according to the present invention.

Possible construction technique to manufacture an ellipsoidal cavity include bonding of metallic patches, use of wire meshes, use of fibreglass molding. In an experimental prototype to test the present invention, a construction technique using the fibreglass method, usually employed in small ship industry to construct boats, was used to manufacture an ellipsoidal cavity with the above selected dimensions. The ellipsoidal structure was split into upper and lower pieces along the major axis to ease the construction process. The inner surfaces of the two half-ellipsoidal shells were painted with a conductive paint to achieve a good reflection of incident electromagnetic waves. To achieve good reflection properties, various paints were tested by using a network analyzer (open waveguide) measurement process. The paint ELCTRODAG 440AS™ Highly Conductive Nickel Coating (Acheson Company) was found to be suitable for this purpose. Interestingly, despite the good conductivity of many paints such as aluminum paint, many failed to provide a satisfactory solution. A cross-section of the ellipsoidal cavity with instrumentation is illustrated in the schematic diagram of FIGS. 4 and 7.

Figure 2:
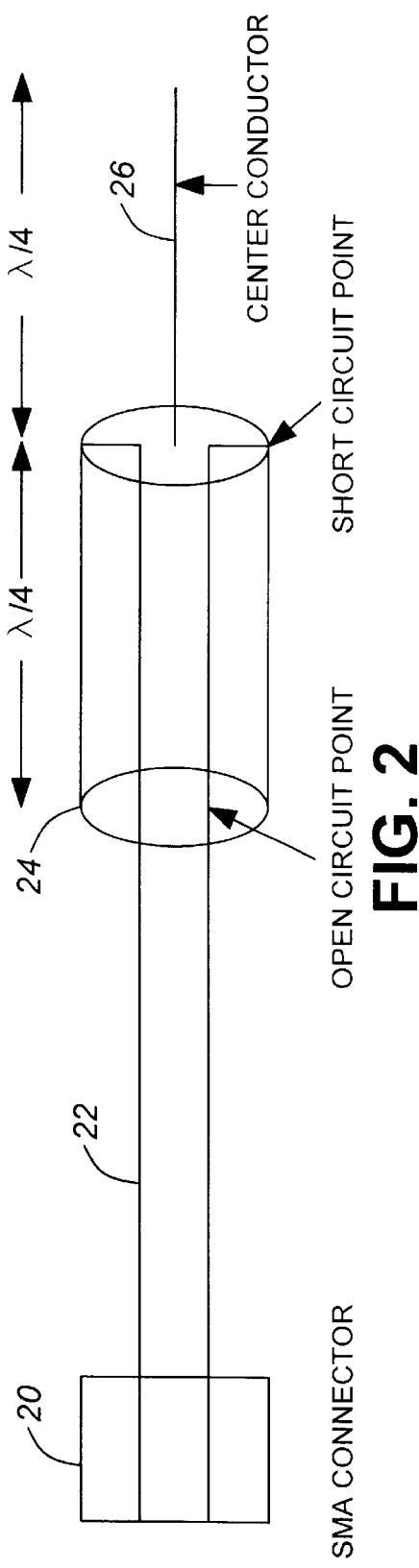
FIG. 2 is a schematic diagram of a sleeved coaxial line dipole antenna for detecting microwaves.
Figure 3:
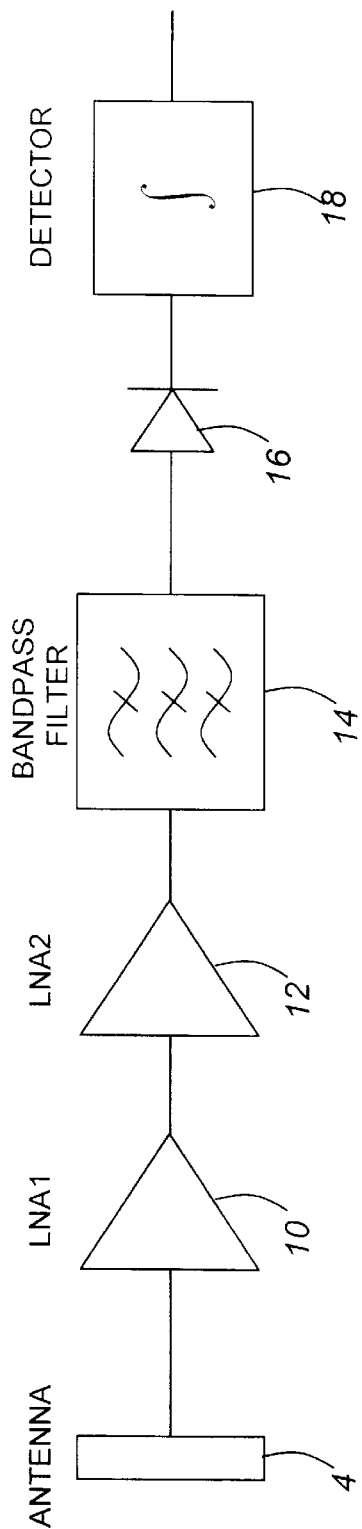
FIG. 3 is a block diagram of a radiometer circuit according to the present invention.

To detect reflected radiation at a focal point ($F_2$ in FIG. 1) of the ellipsoidal cavity, a standard sleeve dipole constructed using a semi-rigid coaxial line as shown in FIG. 2 was used. This was tuned with a network analyzer to achieve good match at the antenna input. A satisfactory 1.5:1 VSWR at a full 400 MHz bandwidth is achieved with this design. It should be particularly noted that the sleeve dipole prevents the induction of surface currents on the coaxial feeding line as it is important not to disturb the radiation pattern on the antenna. The antenna is formed of a SMA connector connected as shown by lines 22 to a $\lambda/4$ length sleeve and a $\lambda/4$ length central conductor 26 as illustrated in FIG. 3. This particular embodiment has a 400 MHz bandwidth but the selected bandwidth could be from about 50 MHz to 400 MHz.

The block diagram in FIG. 3 illustrates the circuit of a total power radiometer according to the present invention with a center frequency of 1.5 GHz or 3.5 GHz and a bandwidth of 400 MHz or 100 MHz, respectively. The signal incident from the antenna 4 is amplified and filtered sequentially. Two identical low noise amplifiers (LNA) 10 and 12 in series are used to raise the detected signal amplitude to compete with the detector shot noise which has an equivalent power of −40 dBm. The detected signal from antenna 4, after amplification, is fed to bandpass filter 14 constructed using a interdigital line to achieve a 400 MHz bandwidth. The signal from the bandpass filter is fed, via a diode, to a detector 18.

The total radiometer microwave frequency gain can be computed by requiring the measured power at the output of the radiometer to be −30 dBm when the radiation from the object at a T=300K equivalent temperature is detected by the antenna 4. The incident radiation to the radiometer is:

$$P_{in} = kTBN_f \quad (4)$$

where k is $1.38 \times 10^{-23}$ J/K,

T is 300 k,

B is $\Delta w/2\pi = 10^8$ Hz is the bandwidth $N_f$(LNA noise figure) is 0.85 dB and then in dBm units:

$$= -173.8 + \lambda + 0.85 = -92.95 \text{ dBm} \quad (5)$$

Therefore the minimum requirement for total gain is $$G = 92.95 - 30 = 62.95 \text{ dB} \quad (6)$$

Figure 4:
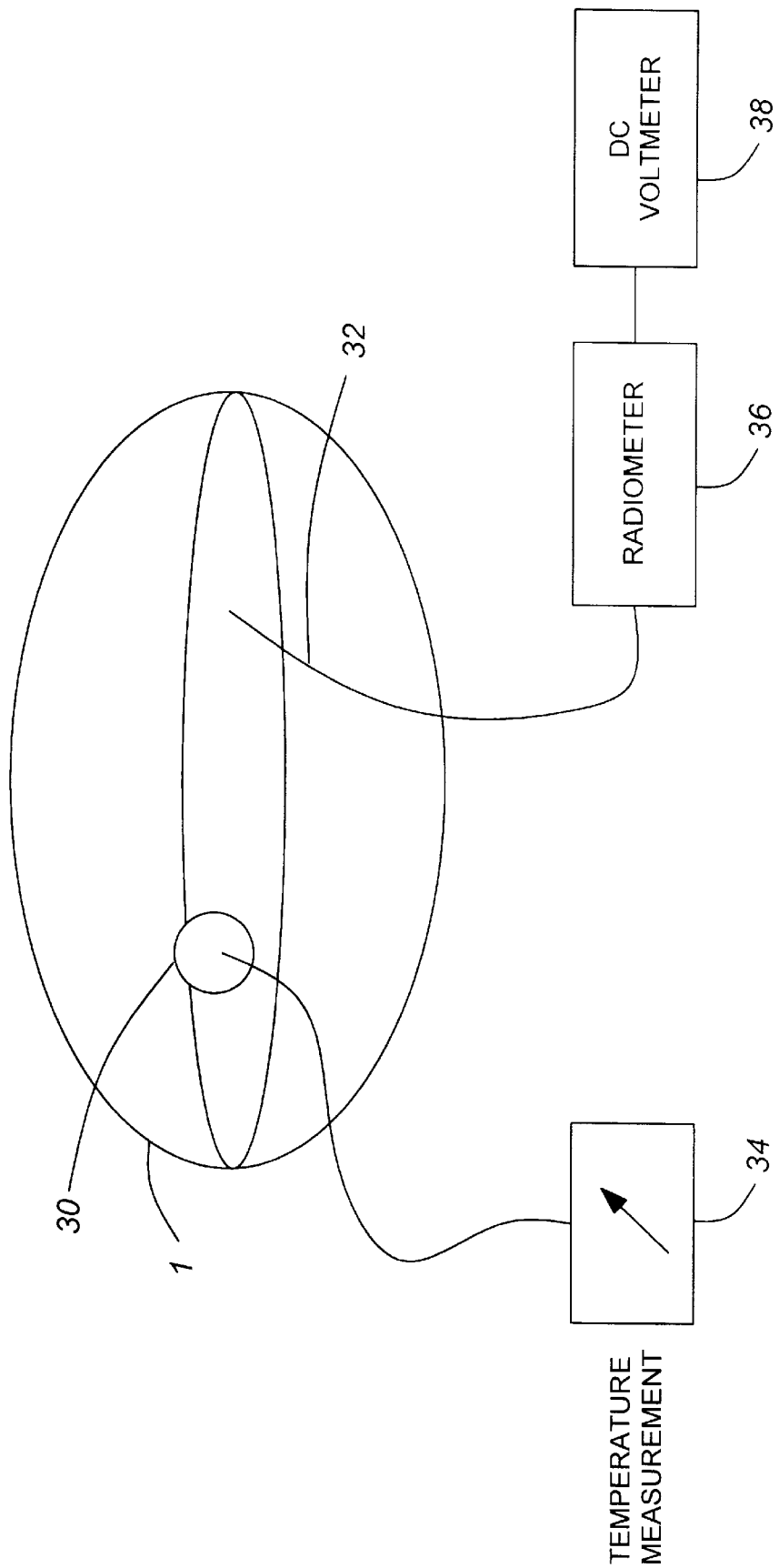
FIG. 4 is a schematic diagram of an experimental set-up to test a microwave thermography system according to the present invention.

The prototype microwave thermography apparatus was arranged as shown in FIG. 4 with a spherical water tank 30 having glass walls (thickness 1 mm) placed at one focus of the ellipsoidal cavity 1 and the sleeved dipole antenna placed at the other focus, as identified by arrow 32, the antenna being connected to radiometer 36. The temperature of the spherical tank filled with hot water can be measured by an LM35 sensor 34 while the output from the radiometer 36 is measured by a DC voltmeter 38. To observe the focusing properties of the ellipsoidal cavity, the spherical tank can be moved mechanically.

Figure 5:
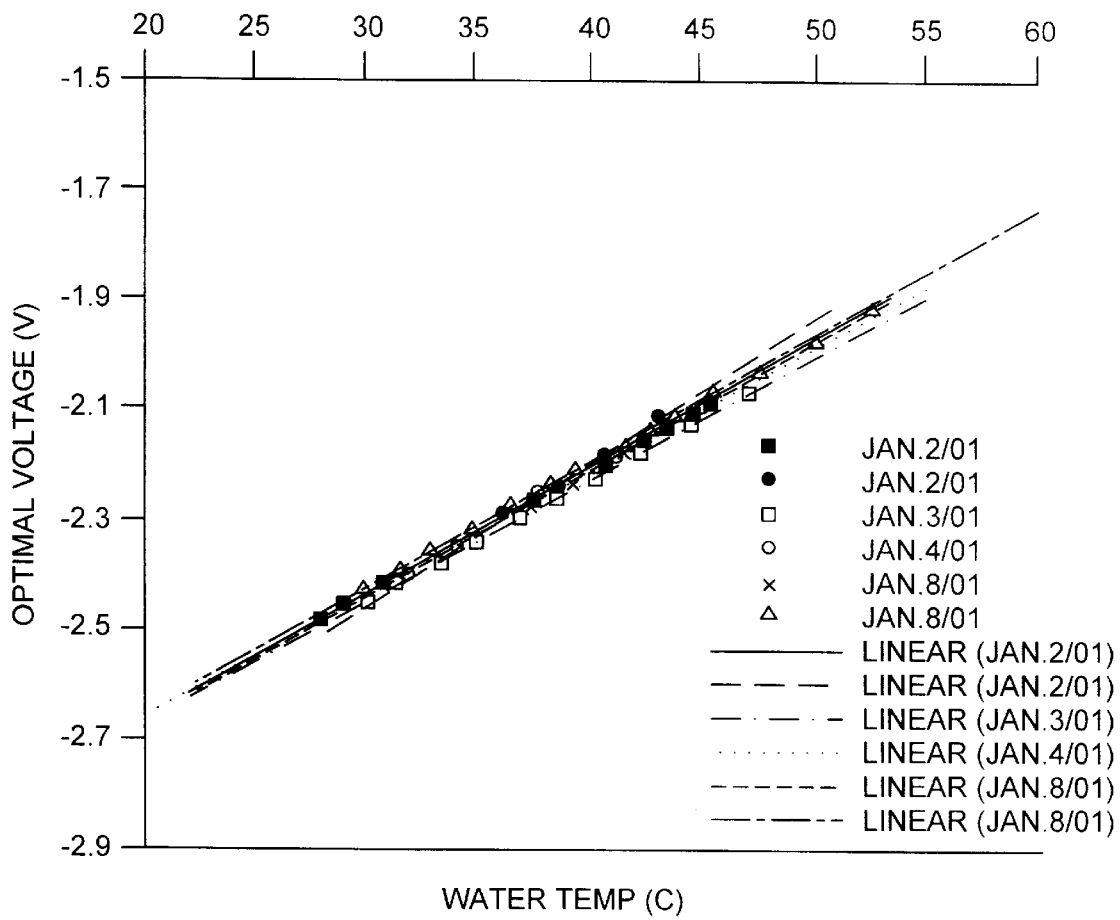
FIG. 5 is a graph showing the variations of radiometer voltage with temperature obtained with the experimental set-up using glass phantoms filled with 0.5, 0.75, 1.0, 1.25 liters of water.

In a first test for this prototype, the glass phantom 30 was filled with various amounts in the range of 0.5 to 1.25 liters hot water at 55° C. and the radiometer output was recorded versus the water temperature as it dropped to environmental temperature. Recorded measurements were made down to 27.5° C. and the variation of radiometer voltage with the temperature is shown in FIG. 5. In FIG. 5, an average slope of 0.0226 mV/°C. was obtained.

Figure 6:
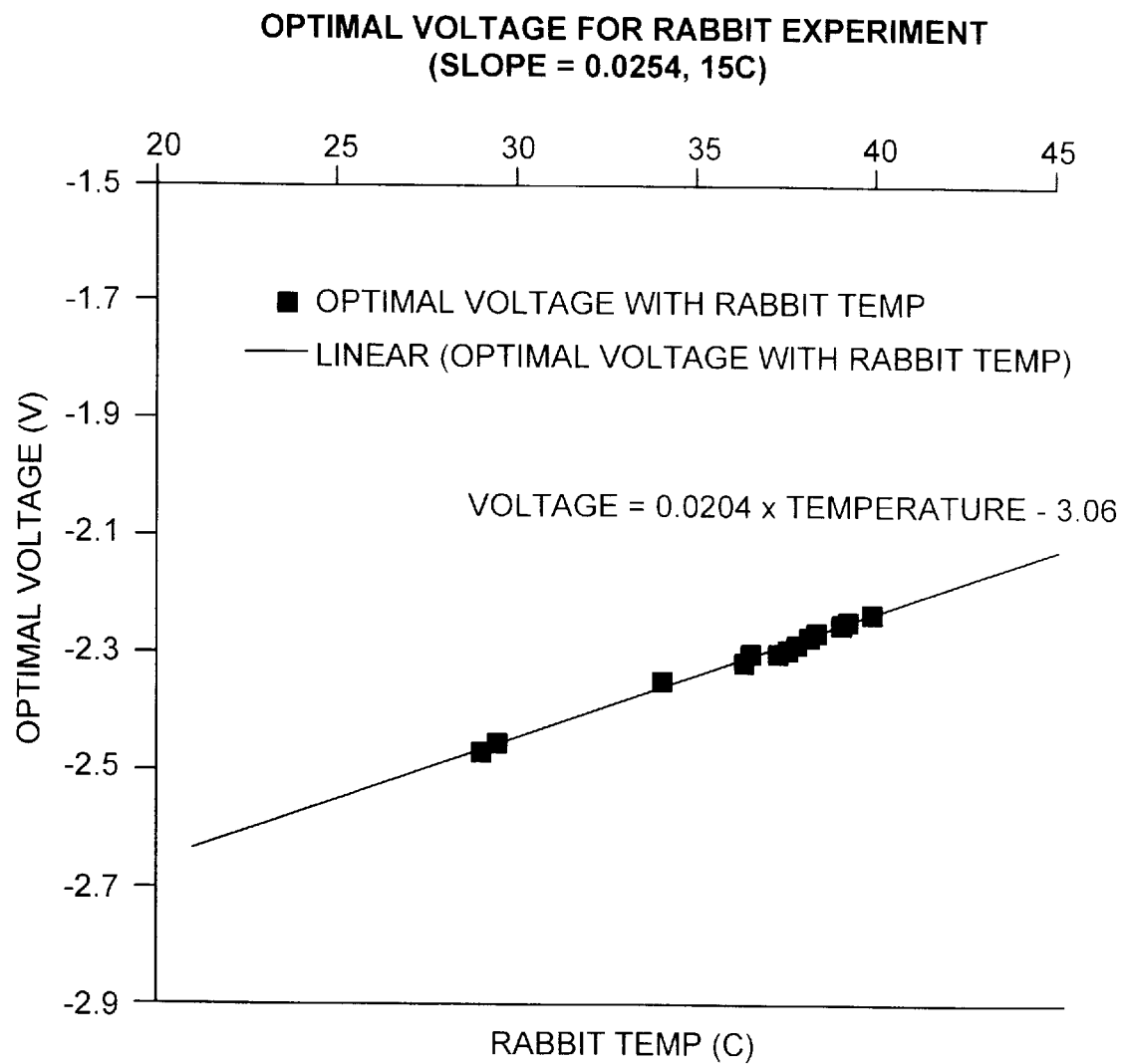
FIG. 6 is a similar graph showing the variations of radiometer voltage for brain core temperature estimates from animal experiments with rabbits.

Similar type of measurements were obtained from animal experiments with rabbits to measure non-invasively brain temperature. FIG. 6 shows the results obtained with the microwave radiometer of the present innovation from the animal experimentation with rabbits. An average slope of 0.0204 mV/°C. was obtained in FIG. 6. The noise at the output of the radiometer was 0.005 mV during the measurements which corresponds to $\delta T = 0.25°$ C. Without the phantom in place, a measurement of 9.2 mV was obtained from the radiometer.

In order to assess the spatial resolution of the prototype, measurements were repeated with the glass phantom moved towards the ellipsoidal cavity center by 15 cm. This allowed an assessment of the microwave radiometer's spatial resolution of 1.5 cm.

The prototype microwave thermography system established that it can measure accurately and on-line temperature inside human head phantoms. Based on measurements carried out, the prototype system operating at the 1.5 GHz or 3.5 GHz frequencies is able to obtain a spatial resolution of ±1.5 cm and a temperature measurement accuracy of ±0.25° C. In fact, this ellipsoidal cavity microwave thermography system has the potential to be able to measure the three dimensional temperature distribution inside the human body including the human skull for intracranial diagnostic brain applications or within any opaque dielectric. Furthermore, it is emphasized that these systems can accomplish those measurements in almost real time since only 1–2 sec integration times would be required. To measure the temperature within a human head an opening would have to be located in one half of the ellipsoidal cavity 1' as illustrated in the FIG. 7 block diagram so that the human head could be located at one focus and be movable about that focus. Therefore, an actual system would utilize a partial ellipsoidal cavity having an electrically conductive inner wall. This would require an ellipsoidal cavity 1' with a relatively large size such as 1.5 m (major axis) and 1.0 m (minor axis).

Considering the fact that the temperature distribution inside the human body is a fundamental physiologic parameter, the following possible applications for clinical use of this type of system can be listed.

1. Measurement of temperature within the human brain such as in the thalamus in association with the measurement of event related brain potentials in physiology studies.

2. Detection of breast cancer by exploiting the very high spatial focusing properties of the ellipsoidal cavity.

3. Measurement of temperature variation within abdomen and pelvic region can be highly useful.

4. Measurements by a non-invasive device for brain temperature would aid in the clinical treatment of the following conditions:
   head trauma
   heat stroke
   brain hemorrhages (eg. from aneurysm rupture)

patients at risk of stroke from any of the above conditions intra-operative monitoring of hypothermia in cerebrovascular surgery (eg. during carotid endarterectomy, the surgeon may ask for cerebral hypothermia as a mechanism to protect the brain from stroke when the internal carotid artery is temporarily occluded as the atherosclerotic plaque is removed from inside it).

Furthermore, this type of microwave thermography system can provide the answer to the issue of mobile phone effects on the human brain.

The described system is open to many improvements to become an effective clinical diagnostic device for a variety of medical applications, such as:

(a) development of a moving table which will allow the movement of a human body and the measurement of the spatial distribution of the temperature field within the body;

(b) improvement of the receiving antenna such as by using multi-polarization wideband dipoles or conical dipoles as these are expected to improve temperature measurement accuracy; and (c) the development of a fully automatic system incorporating a three axis measurement of the human body and recording automatically the three dimensional temperature.

(d) The development of a small helmet size ellipsoidal cavity for mobile use in search and rescue operations, ambulances and emergency departments of hospitals to cover requirements for non-invasive measurements of average temperature of the human brain.

Various modifications may be made to the described embodiment without departing from the spirit and scope of the invention as defined in the appended claims. If one is interested in only measuring the average temperature of the human brain, rather than the three dimensional temperature distribution, a more compact elliptic or other type of cavity (size of a helmet) to carry out the temperature measurement may be used.

The embodiments of the invention in which an exclusive property or privilege is claimed are defined as follows:

1. A microwave thermography apparatus to measure temperatures within a dielectric body, the apparatus comprising a partial ellipsoidal cavity having an electrical conductive surface wherein the body can be inserted through an opening in the ellipsoidal surface and located at one focus of the cavity, a microwave antenna being located at a second focus of the cavity with that antenna being connected to a radiometer that amplifies and filters microwave signals from the antenna before those signals are applied to a detector connected to an output of the radiometer.

2. A microwave thermography apparatus as defined in claim 1, wherein the antenna and radiometer operate near a center frequency of between 1.5 GHz to 5 GHz with a bandwidth of about 50 MHz to 400 MHz.

3. A microwave thermography apparatus as defined in claim 2, wherein the opening through which the body can be located at one focus is of a size such that the body is moveable within the cavity allowing different parts of said body to be positioned at said one focus.

4. A microwave thermography apparatus as defined in claim 1, wherein the microwave antenna is a sleeved dipole formed with a coaxial line.

5. A microwave thermography apparatus as defined in claim 1, wherein the microwave antenna is a multi-polarization wide band dipole.

6. A microwave thermography apparatus as defined in claim 1, where the microwave antenna is a conical dipole.

7. A microwave thermography apparatus as defined in claim 2, wherein the microwave antenna is a sleeved dipole formed with a coaxial line.

8. A microwave thermography apparatus as defined in claim 2, wherein wherein the microwave antenna is a multi-polarization wide band dipole.

9. A microwave thermography apparatus as defined in claim 2, where the microwave antenna is a conical dipole.

10. A microwave thermography apparatus as defined in claim 3, wherein the microwave antenna is a sleeved dipole formed with a coaxial line.

11. A microwave thermography apparatus as defined in claim 3, wherein the microwave antenna is a multi-polarization wide band dipole.

12. A microwave thermography apparatus as defined in claim 3, where the microwave antenna is a conical dipole.

13. A microwave thermography apparatus as defined in claim 1, wherein the electrical conductive surface is a highly conductive nickel paint applied to a substrate that is shaped to form said ellipsoidal cavity.

14. A microwave thermography apparatus as defined in claim 2, wherein the electrical conductive surface is a highly conductive nickel paint applied to a substrate that is shaped to form said ellipsoidal cavity.

15. A microwave thermography apparatus as defined in claim 3, wherein the electrical conductive surface is a highly conductive nickel paint applied to a substrate that is shaped to form said ellipsoidal cavity.

* * * * *

UNITED STATES PATENT AND TRADEMARK OFFICE
CERTIFICATE OF CORRECTION

PATENT NO. : 6,543,933 B2
DATED : April 8, 2003
INVENTOR(S) : Stergiopoulos et al.

It is certified that error appears in the above-identified patent and that said Letters Patent is hereby corrected as shown below:

Column 3, line 59 - Column 4, line 2,
Should read:

where:
$\omega_o$ is the center frequency (in radians/sec) of the observed microwave spectrum bandwidth,
$\mu_o$ is the magnetic permeability constant,
k is Boltzaman's constant,
$\Delta\omega$ is the bandwidth of observed microwave spectrum,
$T(\underline{r}_A)$ is the temperature spatial distribution within the medium of interest, and
$\sigma(\underline{r}_A)$ is the spatial distribution within the medium of interest for the electric conductivity.

Lines 43-56, should read:

The intensity of the radiation field defines the requirement associated with the measurement of 3-D temperature inside a lossy medium. It can be shown that in order to have a satisfactory spatial resolution for a microwave thermography device, that:

$$\Gamma_A(\underline{r}') \sim c_t \delta(\underline{r}_A - \underline{r}') \qquad (1)$$

where $\Gamma_A(\underline{r}')$ is the transfer function for the medium, $\underline{r}_A$ is the antenna center coordinates, $\underline{r}'$ is the coordinates of the microwave originating area and $c_t = 3 \times 10^8$ m/sec is a constant. Then the analytical solution for the total radiated energy by the medium defined in (1) gives the intensity $$I = \frac{\omega_o^2 \mu_o k}{\pi} \Delta\omega \cdot c_t T(\underline{r}_A) \sigma(\underline{r}_A) \qquad (2)$$

UNITED STATES PATENT AND TRADEMARK OFFICE
CERTIFICATE OF CORRECTION

PATENT NO. : 6,543,933 B2
DATED : April 8, 2003
INVENTOR(S) : Stergiopoulos et al.

It is certified that error appears in the above-identified patent and that said Letters Patent is hereby corrected as shown below:

<u>Column 4,</u>
Lines 3-12, should read:

The present invention can provide estimates of the product of $T(\underline{r}_A)\sigma(\underline{r}_A)$. Since the electric conductivity spatial distribution is approximately constant within the brain tissue structure, estimates of product term $T(\underline{r}_A)\sigma(\underline{r}_A)$ by the apparatus of the present invention will provide estimates of the temperature distribution within the intracranial cavity or any medium of interest. An exact assessment would require an extensive and rigorous analysis of the corresponding electromagnetic problem. Therefore, a geometrical optics approach is used herein to estimate the resolution properties of the present invention.

<u>Column 5,</u>
Line 59, should read:
    -- P = -173.8 + 80 + 0.85 = -92.95dBm           (5) --

Signed and Sealed this

Twenty-sixth Day of August, 2003

JAMES E. ROGAN
*Director of the United States Patent and Trademark Office*